US007951109B2

(12) United States Patent
Anderson

(10) Patent No.: US 7,951,109 B2
(45) Date of Patent: May 31, 2011

(54) LIQUID CHAMBER CAP WITH COMPARTMENT FOR USE WITH INJECTABLES

(75) Inventor: Michael R. Anderson, Arroyo Grande, CA (US)

(73) Assignee: Andeboh Holdings, FLP, Carson City, NV (US)

( * ) Notice: Subject to any disclaimer, the term of this patent is extended or adjusted under 35 U.S.C. 154(b) by 101 days.

(21) Appl. No.: 11/534,458

(22) Filed: Sep. 22, 2006

(65) Prior Publication Data

US 2008/0125704 A1 May 29, 2008

(51) Int. Cl.
*A61M 39/20* (2006.01)
*B65D 39/00* (2006.01)

(52) U.S. Cl. ............ 604/87; 604/88; 604/415; 604/416; 222/83; 215/251; 215/256; 206/222

(58) Field of Classification Search ............. 604/167.01, 604/167.02, 167.03, 167.04, 167.06, 180, 604/236, 238, 533, 539, 905, 33, 93.01, 237, 604/87–88, 415–416; 222/80–91, 83.5, 541.2; 215/297, 6, 257, 247; 220/521–523, 267; 206/219, 222

See application file for complete search history.

(56) References Cited

U.S. PATENT DOCUMENTS

| | | | | |
|---|---|---|---|---|
| 4,230,584 | A * | 10/1980 | Ichikawa et al. | 210/516 |
| 4,747,501 | A * | 5/1988 | Greaves | 215/253 |
| 4,982,875 | A * | 1/1991 | Pozzi et al. | 222/83 |
| 5,038,951 | A * | 8/1991 | Rizzardi | 215/256 |
| 5,782,345 | A * | 7/1998 | Guasch et al. | 206/222 |
| 5,811,060 | A * | 9/1998 | Laguna Valderrama | 422/102 |
| 6,116,445 | A * | 9/2000 | Ikemori et al. | 215/301 |
| 6,145,688 | A * | 11/2000 | Smith | 220/259.3 |
| 7,325,676 | B2 * | 2/2008 | Galaz Rodriguez | 206/219 |
| 2004/0020797 | A1 * | 2/2004 | Fontana | 206/219 |
| 2005/0161348 | A1 * | 7/2005 | Morini | 206/219 |

* cited by examiner

*Primary Examiner* — Nicholas D Lucchesi
*Assistant Examiner* — Quynh-Nhu H Vu
(74) *Attorney, Agent, or Firm* — Malin Haley DimMagio Bowen & Lhota, P.A.

(57) ABSTRACT

A storage and dispensing cap for a liquid receptacle having a cap body storage chamber for use with a receptacle such as a bottle, pouch or intravenous bag that is used to store a liquid for use with a syringe that is inserted into the receptacle for drawing the liquid contents into the syringe. A liquid, powder or capsule in the cap body chamber is mixed into the liquid receptacle for use with the syringe. A sleeve penetrator is mounted inside said cap body chamber and is sized in length to permit rupture of the bottom floor of said cap body chamber when manually depressed for dispensing whatever material is placed inside said cap body chamber and sleeve penetrator into said syringe bottle. An open passage from the cap body to the inside of the receptacle is provided once the storage chamber is ruptured by manually depressing the penetrator to allow the syringe needle end to be inserted into the liquid receptacle.

5 Claims, 6 Drawing Sheets

LIQUID CHAMBER CAP WITH COMPARTMENT FOR USE WITH INJECTABLES

BACKGROUND OF THE INVENTION

1. Field of the Invention

A liquid and/or dry ingredient dispensing cap that can be mounted to a pharmaceutical substance container or receptacle such as a bottle, pouch, syringe test tube or any container that can hold a liquid for storing injectable pharmaceuticals or any other ingredients used for injection into a human being.

2. Description of Related Art

Many pharmaceuticals and other substances do not retain their stability, strength and effectiveness for long after the ingredients have been mixed in solution or suspension with a different liquid. This reduced shelf life after mixing mandates that the mixed product be utilized relatively soon after mixture to obtain full strength to prevent loss of effective strength, deterioration, discoloration, interactions and reduced effectiveness. The process of loss of chemical effectiveness is often termed "shelf life." Once two different chemicals are combined, the process of deterioration begins. One area of concern with shelf life and product effectiveness deals with pharmaceuticals. Certain drugs begin to lose their effectiveness when mixed together and thus have a short shelf life. Many drugs are dispensed by injection using a hypodermic needle or a syringe. An injectable drug to be dispensed may come in an individual sealed chamber having a sealed penetrable top that permits introduction of a syringe that pierces the sealed top material. Once the needle top is deep inside the chamber, the drug is drawn into the syringe chamber for injection. It is also important that admixtures of various ingredients be done under conditions where a measured amount of one ingredient is added to a measured amount of another liquid or chemical to ensure that proper results are obtained.

A dispensing cap for a container used to store injectable substances that can accept a syringe for loading the syringe. The cap includes its own substance storage and dispensing chamber. The substance stored in the cap can be dispensed into the injectable container for mixing with the container contents. The shelf life of the combined injectable substance is extended indefinitely. The syringe injectable container cap can be used as a storage chamber for a substance that can be admixed with another substance that is stored in the primary container.

SUMMARY OF THE INVENTION

A cap for dispensing one or more ingredients into a bottle, pouch, I.V. bag or other container or liquid receptacle used for housing pharmaceuticals for injectable syringes. The cap body includes a substance storage chamber having a frangible or tearable base. The cap body also includes a top peripheral lip that acts as a stop when placed over a receptacle opening such as a bottle neck or other type of injectable liquid holding device. A sleeve-shaped penetrator is disposed inside said cap body chamber. The penetrator includes a cutting edge along its bottom perimeter.

A sealable cover is attached to the cap body top opening, covering said cap body storage chamber and said sleeve penetrator when not in use. With the sealable cover manually removed and the penetrator manually actuated, the cap body provides an open passage to insert a syringe nozzle into the pharmaceutical containing receptacle having the now mixed ingredients.

The cap body storage chamber can be filled at the factory with a substance to be mixed with the liquid injectable that is also filled at the factory. The substance can be a liquid, powder, gel or other dissolvable chemical.

The sleeve penetrator acts as a reciprocal member that is manually movable downwardly along the longitudinal axis of the cap body storage chamber. The sleeve penetrator is mounted flush on its outside surface against the inside surface of the cap body chamber. Thus, any substance placed in the cap body chamber is surrounded by the sleeve penetrator. The cap body top has an aperture for receiving a syringe. The aperture is covered and sealed with a disc or stop cover before use. The cover is used to enclose and seal the sleeve penetrator and the cap body to protect the contents of the chamber from contamination. A stop cover can be a rubber or rubber like material that is a plug covering the cap body chamber top aperture through which a needle tip can be inserted.

The substance or substances in the cap body chamber can be dispensed into the receptacle containing a different pharmaceutical. After admixing, the mixed substances in the receptacle can be drawn into a syringe that is inserted through the cap body into the receptacle.

To activate and mix, the sleeve penetrator is manually depressed to such an extent that its lower cutting edge penetrates the cap body chamber bottom surface, ripping the bottom downwardly, causing the contents in the cap body chamber to be dispensed through the ripped chamber bottom opening caused by the sleeve penetrator and into the syringe pharmaceutical container, mixing with the contents of the container. The chamber bottom surface could include a line of weakening for tearing easier.

Once the contents of the cap body storage chamber have been thoroughly mixed with the contents of the syringe injectable liquid container and the admixture is ready to be drawn into the syringe, the sealable cover may be removed from the top of the cap body or penetrated by the syringe needle end point to draw the mixed contents in the syringe. The cap body chamber can be made of a sealable metal foil, rubber or plastic material so that the syringe can be forced through the rubber or plastic stop or manually removed.

The sleeve penetrator is hollow throughout. The diameter of the sleeve penetrator is large enough to accommodate almost any conventional syringe diameter that is extended through the cap body into the syringe injectable receptacle. A user can manually position the syringe through the sleeve penetrator passage. The syringe end point can be easily maneuvered into the bottle for removing the mixed contents of the injectable container and transferring the contents into the syringe in a conventional manner.

In an alternate embodiment, the present invention and cap body with a storage chamber can also be used with a drinking straw and a conventional beverage container, without using a syringe. When the scalable cover is removed and the sleeve penetrator activated, mixing the contents of the cap body chamber with the contents of the liquid receptacle or bottle, a straw can be inserted through the cap body passage so that the user can drink the mixed contents of the bottle by inserting the straw through the passage in the bottle cap.

In another use without a straw, there is a sufficient passage through the bottle cap after the sleeve penetrator has been activated and the foil seal removed so that one can drink directly from the container with the mixed contents.

It is an object of this invention to provide an improved cap for a bottle, pouch, I.V. bag or receptacle that houses a syringe injectable liquid that stores a second substance for admixing.

It is another object of this invention to provide a primary liquid receptacle cap having a storage chamber for a substance to be mixed with the primary liquid and consumed through a straw or directly from the primary receptable.

In accordance with these and other objects which will become apparent hereinafter, the instant invention will now be described with particular reference to the accompanying drawings.

PREFERRED EMBODIMENT OF THE INVENTION

Figure 1:
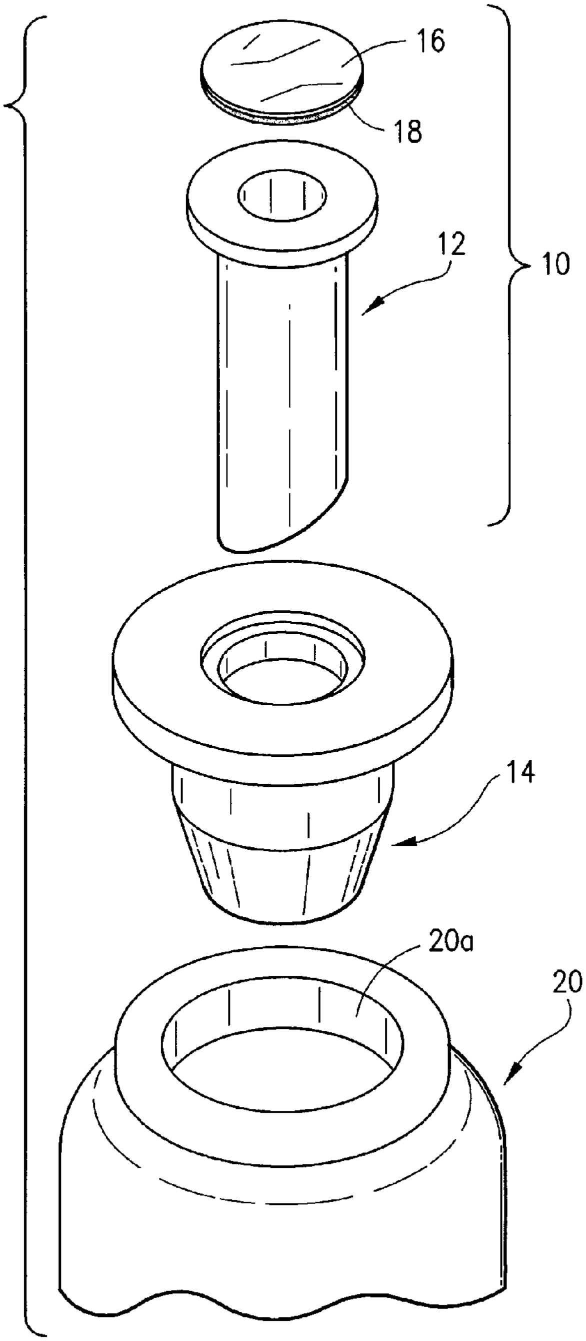
FIG. 1 shows an exploded perspective view of a container cap for a container housing an injectable substance to be used for filling a syringe.

Referring now to FIG. 1, an injectable container cap 10 is shown comprised of a molded plastic cap body 14, a sleeve penetrator 12 and sealable cover 16 positioned above an injectable substance container 20 having a container neck opening 20*a*.

The sleeve penetrator 12 is a rigid plastic cylinder that is hollow and has a central passage there through. The lower end of the sleeve penetrator 12 is cut at an oblique angle to the longitudinal axis which allows the lower end or base of sleeve penetrator 12 to penetrate through the bottom floor of cap body 14 as described below.

A sealable disc-shaped protective cover 16 has adhesive 18 coated on certain portions on the cover 16 bottom, which allows the cover 16 to be adhesively attached and sealed to the top lip of sleeve penetrator 12. The cover 16 could be made of metal, foil, plastic, rubber or a rubber like material formed as a plug through which a needle can penetrate.

One purpose of the invention is to allow someone that is about to fill a syringe with a therapeutic liquid to be able to dispense a separate liquid, powder, or capsule into the therapeutic liquid in the syringe container housing the injectable pharmaceutical so that the two ingredients can be combined just prior to drawing the mixed ingredients into the syringe compartment prior to injection into a person.

The advantage of being able to combine one ingredient such as a liquid, powder or capsule that dissolves within the second liquid is to preserve the shelf life and the efficacy of the combined ingredients for therapeutic value. An access passage is provided through the cap body and storage chamber that once activated allows a syringe end to be easily positioned within the primary container after the ingredients have been effectively mixed for ease in drawing the mixed ingredients into the syringe.

Figure 2:
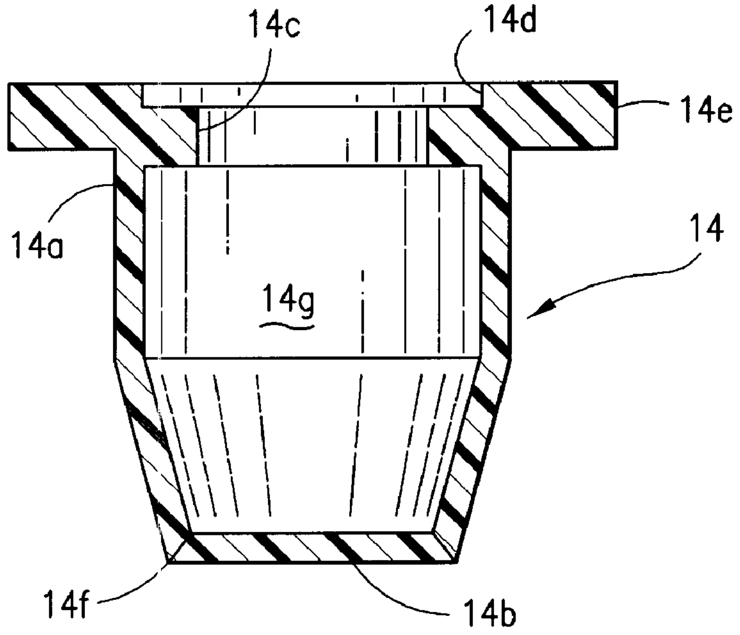
FIG. 2 is a side elevational view in cross section of the cap body and chamber.

Referring now to FIG. 2, the cap body 14 is shown that includes a plastic water or liquid-proof cylindrical wall section that may be slightly tapered towards the bottom to allow the cap body chamber to fit snuggly in the primary container opening. This allows cap 14 to be positioned within the container opening 20*a* (FIG. 1) as a sealed member.

Cap body 14 includes an ingredient storage chamber 14*g*. The bottom wall or floor 14*b* of cap body 14 storage chamber 14*a* may be structured so that along the edge of the base 14*f* where the floor 14*b* meets the cap body 14*a*, there can be one or more lines of weakening that allows the floor 14*b* to be penetrated and ruptured by the sleeve penetrator 12 (shown in FIG. 3).

The upper cap body 14*e* provides a lip or flange that can act as a seal in a container opening 20*a* (FIG. 1). The cap body 14 also includes a passage 14*c* that receives the sleeve penetrator 12 which is described below. The upper cap body 14*e* also includes a recess 14*d* that can engage lip 12 to stop the penetrator 12 when pushed so that the penetrator will not fall into the primary container having the syringe injectable.

Figure 3:
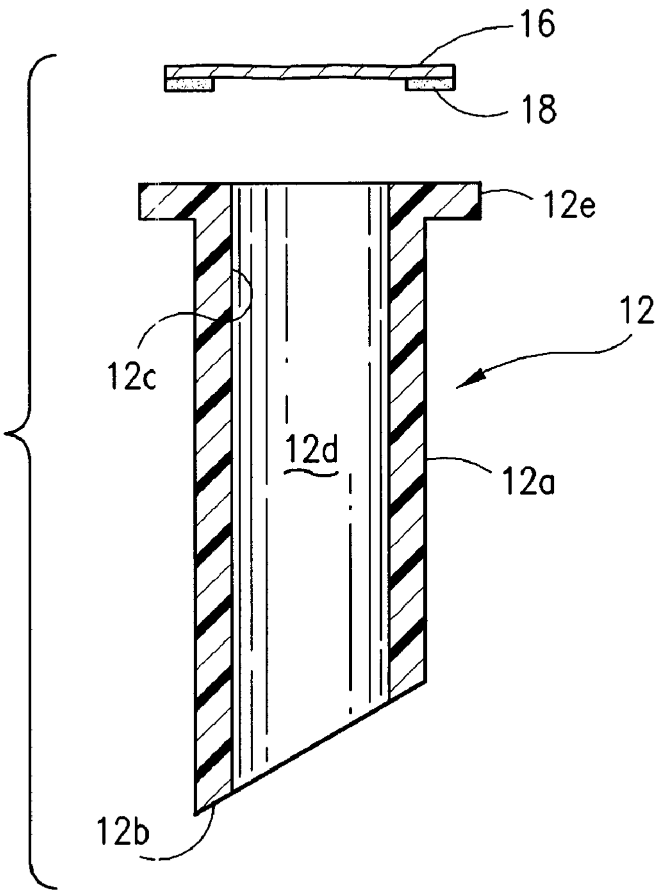
FIG. 3 is an exploded side elevational view of the sleeve penetrator and foil cap.

Referring now to FIG. 3, the sleeve penetrator 12 is a rigid cylindrical tube having an angularly cut base 12*b* at a sharp angle compared to a perpendicular to the longitudinal axis. The sleeve penetrator 12 includes a lip 12*e* that stops downward movement when the cap is activated for dispensing an ingredient from storage chamber 14*g*.

A protective liquid-proof cover 16 is used with adhesive 18 for gluing the cover 16 over the top opening of passage 12*c* so that the entire cap body chamber 14*g* is sealed.

Figure 4:
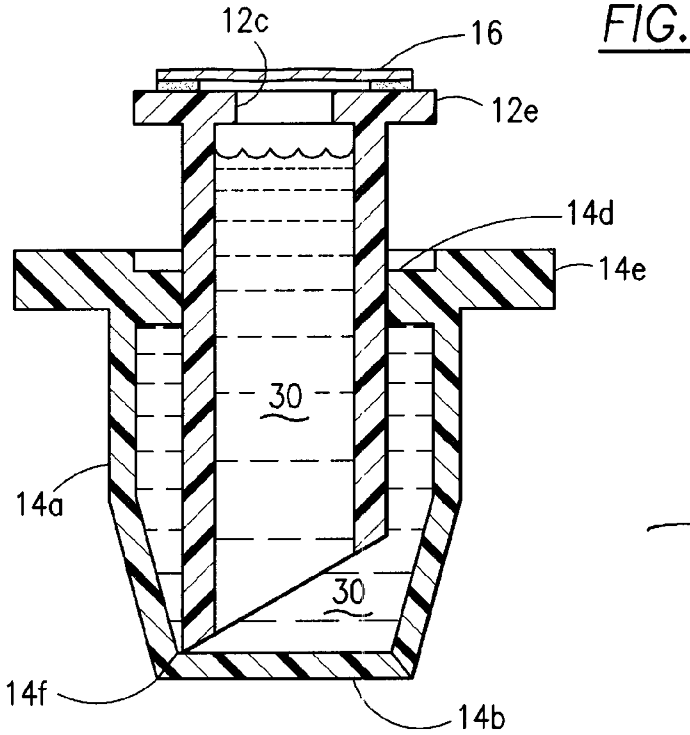
FIG. 4 is a side elevational view in cross section showing a cap filled with a substance prior to dispensing the substance into a container.

Referring to FIG. 4, the dispensing cap 10 for the chamber 20 (FIG. 1) is shown filled with a liquid substance 30, all of which is sealed within the cap body chamber 14*a* with the bottom 14*b* being sealed and with a sealed cover 16 glued over the sleeve penetrator 12 opening 12*c*. In this configuration, the entire cap 10 is inserted and sealed into the primary container 20 housing an injectable substance shown in FIG. 1. The cap 10 in FIG. 4 has not been manually activated.

Figure 5:
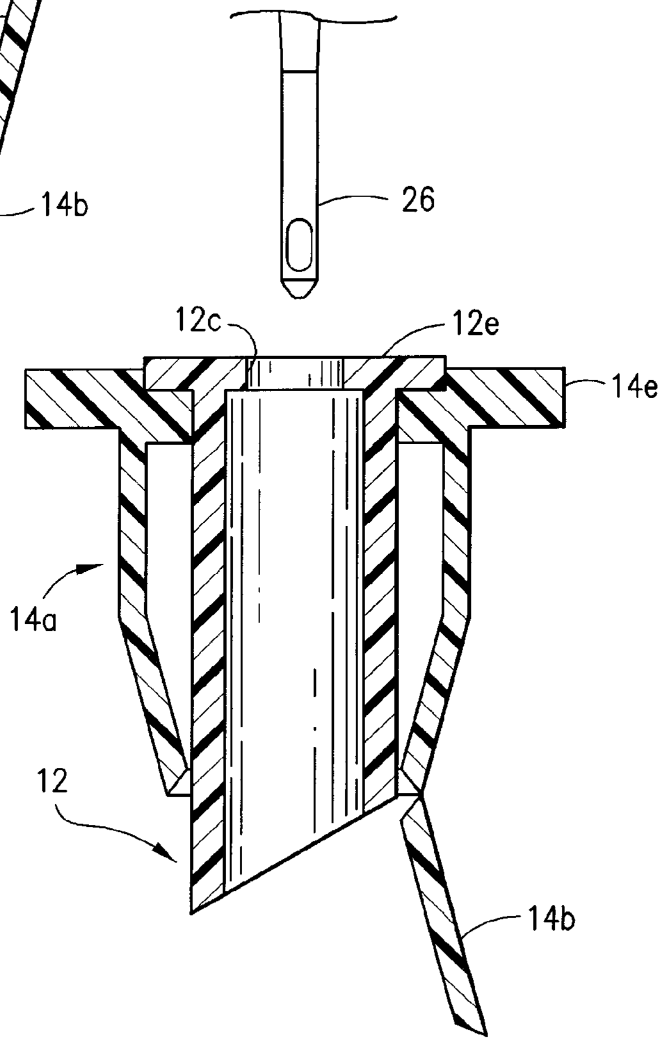
FIG. 5 shows an elevational view in cross section after the sleeve penetrator has been activated, dispensing the substance located inside the cap body, with a cut away view of a syringe tip adjacent the opening in the cap.

Referring now to FIG. 5, the sleeve penetrator 12 has been pushed manually downwardly, rupturing the floor 14*b* of cap 14 allowing liquid 30 to be dispensed into the primary container 20 (FIG. 1). A syringe tip 26 is shown suspended above sleeve penetrator opening 12*c*. The chamber bottom floor 14*b* has been severed.

Figure 6:
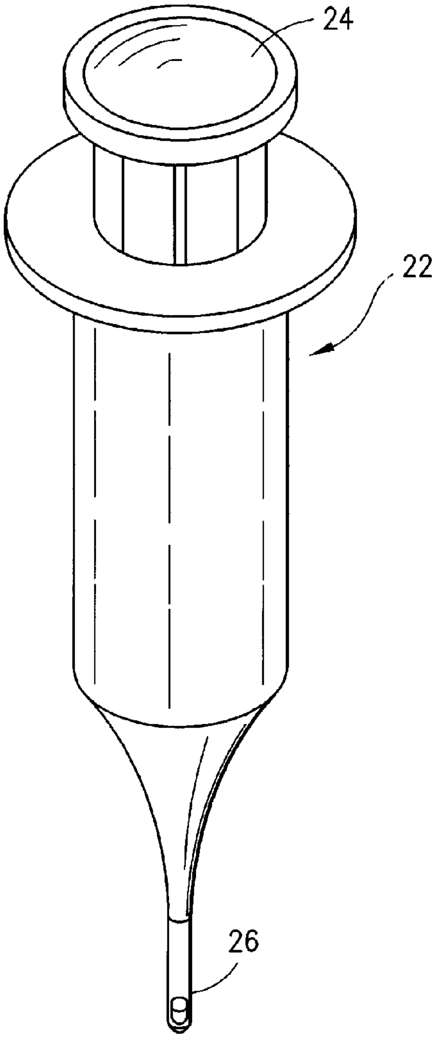
FIG. 6 shows a conventional syringe that could be used.

FIG. 6 shows a conventional syringe 22 that has a drawing piston 24 and the syringe tip 26. The drawing end tip of syringe 22 can be manually placed through cap 14 into primary chamber 20 after the cap chamber 14*g* has been ruptured and the cover removed.

Referring back to FIG. 4, the penetrator 12 includes a lip 12*e* to stop the downward movement once the base has been ruptured. In an alternate embodiment, the penetrator 12 could have the lip 12*e* removed so that its exterior is flush with the top of the cap and when depressed moved downwardly rupturing the base.

Figure 7:
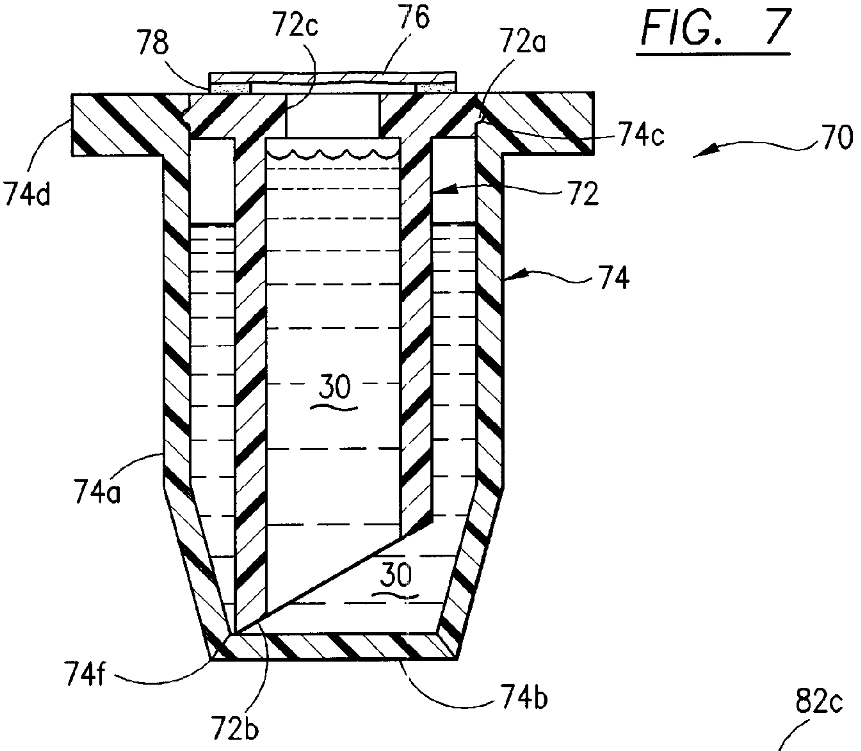
FIG. 7 shows an alternate embodiment of the cap in a perspective view.

Referring now to FIG. 7, an alternate embodiment is shown that includes a cap body 74 that houses penetrator 72. The top of penetrator 72 includes an opening 72*c* that is covered by foil 76 and adhesive 78 before use. The top of penetrator 72 includes an annular lip 72*a* that fits into a recessed annular ring 74*c* in the upper opening of the cap body 74. As shown in the closed position, the annular protrusion or flange 72*a* fits snuggly in groove 74*c* so that the penetrator 72 is tightly sealed to the cap body 74. Upon usage of the device, the penetrator 72 is pushed down manually rupturing cap body floor 74*b* dispensing the substance 30 into the main container for admixture. The penetrator opening 72*c* at the top allows for a syringe to be disposed down through the penetrator sleeve into a container for drawing out the mixture.

Figure 8:
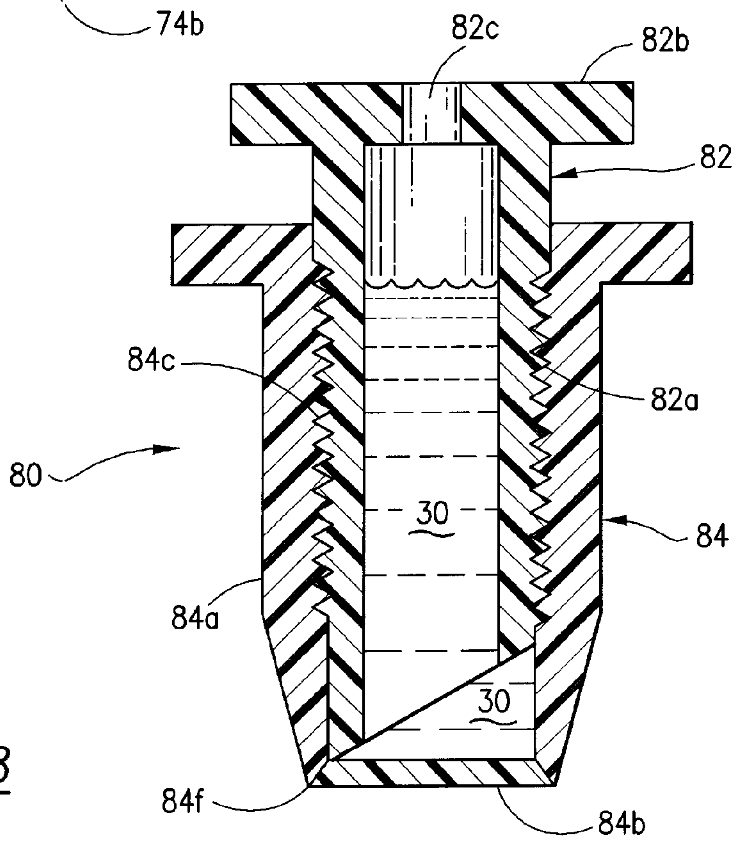
FIG. 8 shows another alternate embodiment of the cap in a side elevational view.

FIG. 8 shows yet another embodiment in which the penetrator 82 includes a plurality of exterior threads 82*a* that engage cap body 84. The inside passage of cap body 84 includes threads 84*c* that engage the penetrator threads 82*a*. The penetrator may include a rubber stop 82*c* that is mounted in the penetrator top 82*b*. The stop 82*c* is of a material that can be penetrated by a syringe needle for usage of the device. To operate the device in FIG. 8, the penetrator 82 is rotated in such a direction forcing the penetrator downwardly through cap body 84 rupturing the floor 84*b* along weakened lines 84*f* dispensing substance 30 into a container for admixture. A syringe needle point is then inserted through plug 82*c*.

Figure 9:
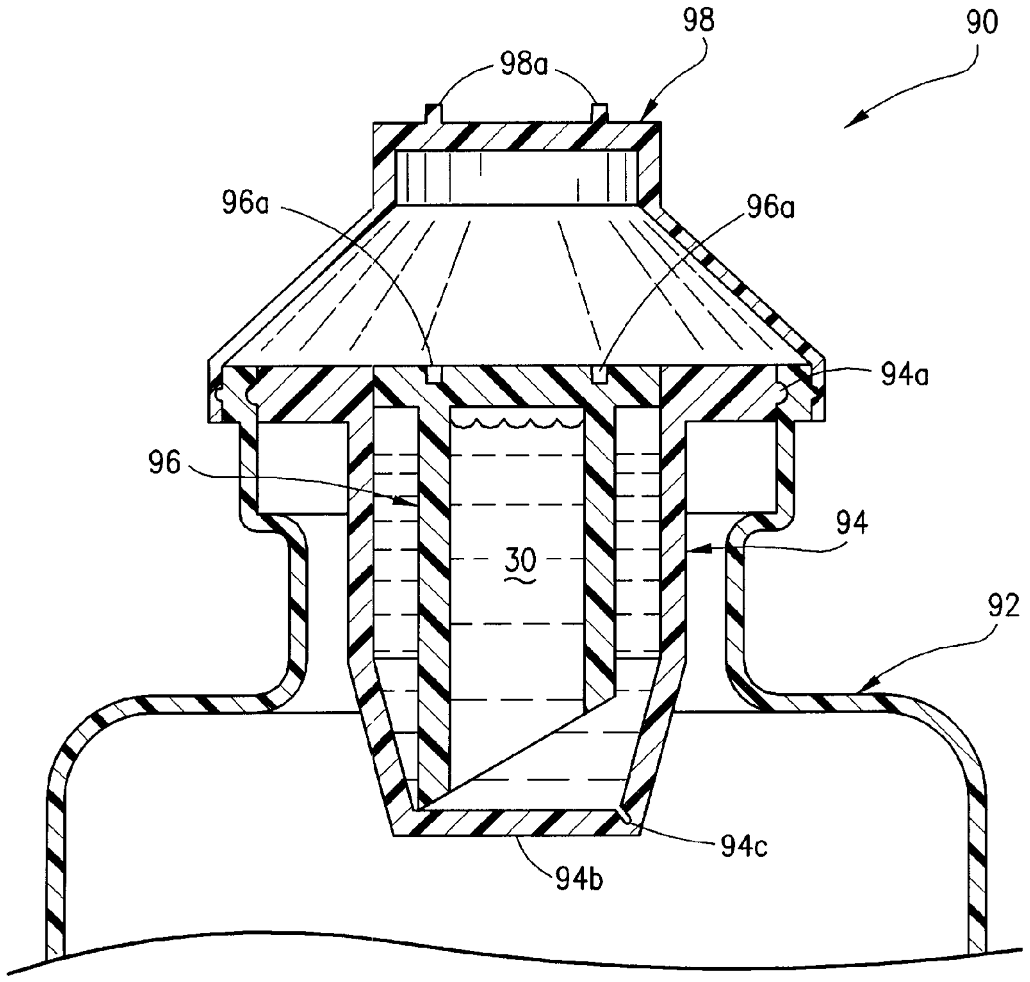
FIG. 9 shows a second mode of operation of the device shown in FIG. 8 in a side elevational view.
Figure 10:
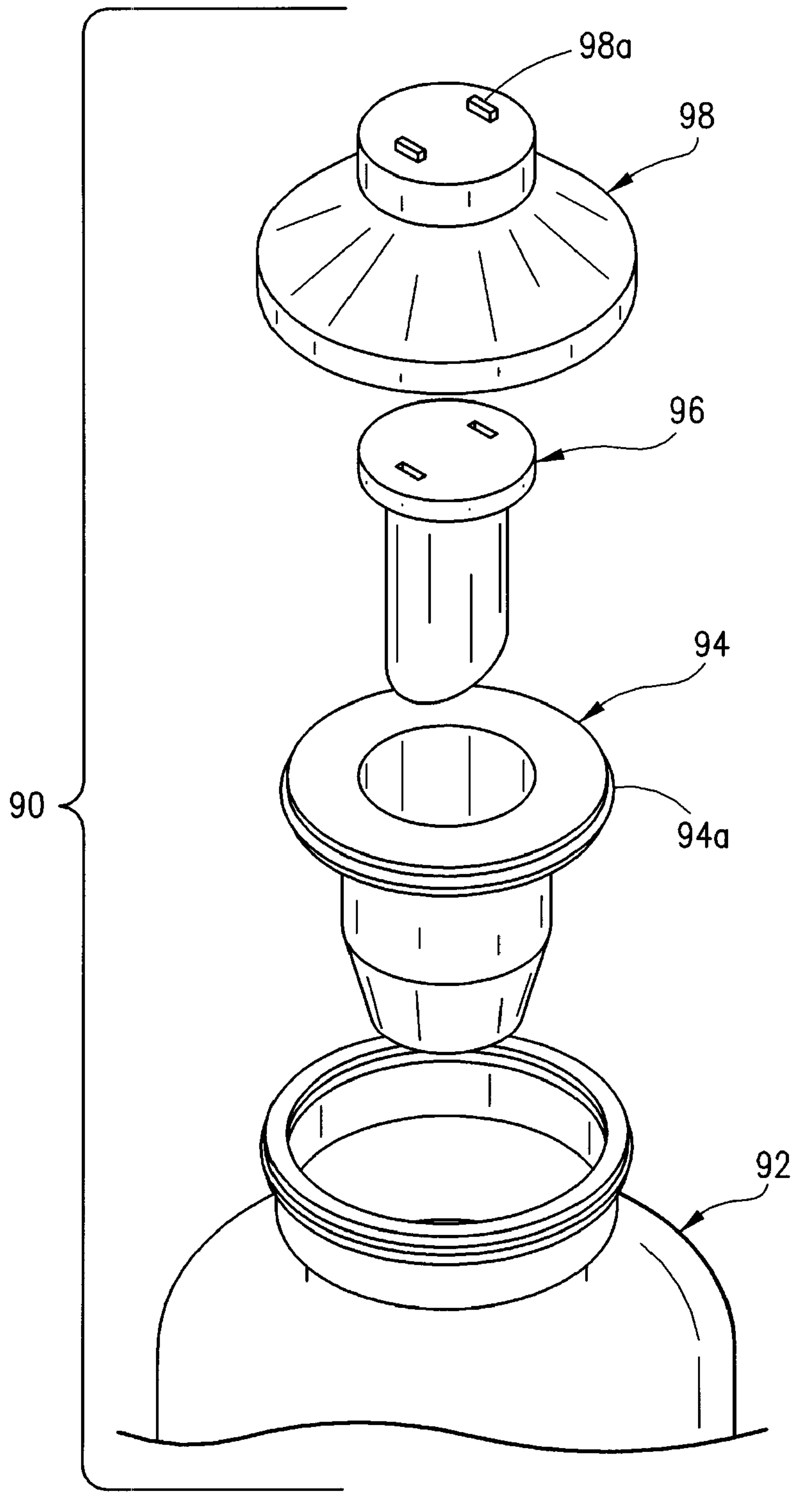
FIG. 10 shows yet another alternate embodiment of the cap in a perspective view utilizing a straw.

FIGS. 9 and 10 show yet another alternate embodiment. The cap body 94 which includes a penetrator 96 having a pair of recessed portions 96*a* in its top is shown mounted on a container 92 as a cap. A dust cover 98 is mounted over the entire cap body and the container opening. When the device is ready for use, the dust cover which includes a pair of protrusions 98*a* is removed from the container 92. The dust cover is then manually inverted and the protrusions 98*a* in the dust cover are engaged into the penetrator recesses 96*a*. The dust cover is then manually pushed downwardly against the penetrator 96 which then ruptures cap body floor 94*b* and weakened line 94*c* dispensing substance 30 into the container for admixture with whatever liquid is in the injectable bottle 92. The dust cover 98 is then disengaged from the penetrator 96. A syringe or needle point to be filled is then manually forced through the top of penetrator 96 into container 92 for drawing out the admix liquid in the container.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A storage and dispensing cap for a liquid receptacle including a bottle, pouch and IV bag that houses a liquid to be utilized and drawn into a syringe;

a cap body including a storage chamber having an open top and a sealed base for holding a liquid, powder or capsule to be dispensed;

a sleeve penetrator connected moveably to said cap body and having a closed top, a hollow interior body and having an outside diameter that is sized to fit snuggly coaxially within and against the inside diameter of said cap body storage chamber open top to permit reciprocal motion between said sleeve penetrator and said cap body storage chamber;

whereby a liquid, powder or capsule can be placed inside said cap body storage chamber and sleeve penetrator hollow body, said sleeve penetrator being depressed to rupture said sealed base of said cap body storage chamber allowing the contents in said cap body storage chamber to be distributed into a liquid receptacle; said sleeve penetrator cover constructed of a material and thickness suitable for penetration by a syringe needle; and a dust cover cap connectable to said cap body over the top of said sleeve penetrator, said sleeve penetrator including rectangular recesses, said dust cover cap including a removable portion that includes a pair of rectangular protrusions for engagement with said rectangular recesses in said sleeve penetrator for plunging the sleeve penetrator downwardly with the removed dust cover cap.

2. A cap as in claim 1, wherein: said cap body chamber sealed base includes a line of weakening that when said sealed base is engaged by said sleeve penetrator said sealed base will easily rupture from said cap body chamber.

3. A receptacle cap as in claim 1, wherein: said sleeve penetrator has a lower base portion that is angled relative to the longitudinal central axis of said sleeve penetrator for rupturing one side of said cap body chamber sealed base.

4. A receptacle cap as in claim 1, wherein: said sleeve penetrator is sized in length and can be depressed below the opening of said bottle cap for rupturing the sealed base of said bottle cap chamber when depressed for dispensing the contents within the cap body chamber to be dispensed into the receptacle.

5. A cap as in claim 1, wherein: said cap including said cap body chamber and sleeve penetrator can be physically mounted anywhere on a liquid receptacle including bottles, pouches and intravenous bags for use with a syringe for drawing out the mixed ingredients.

* * * * *